United States Patent [19]

Eicken et al.

[11] 4,394,513

[45] Jul. 19, 1983

[54] N-AZOLYL ACETANILIDES, THE MANUFACTURE THEREOF, AND THEIR USE AS

[75] Inventors: Karl Eicken, Wachenheim; Wolfgang Rohr, Mannheim; Bruno Wuerzer, Limburgerhof, all of Fed. Rep. of Germany

[73] Assignee: BASF Aktiengesellschaft, Fed. Rep. of Germany

[21] Appl. No.: 108,541

[22] Filed: Dec. 31, 1979

[30] Foreign Application Priority Data

Jan. 17, 1979 [DE] Fed. Rep. of Germany ....... 2901593

[51] Int. Cl.³ .............................................. C07D 403/12
[52] U.S. Cl. .................................... 548/374; 548/262; 548/336; 548/378; 548/341; 71/92
[58] Field of Search .............. 548/378, 374, 262, 336, 548/341

[56] References Cited

U.S. PATENT DOCUMENTS 3,442,945  5/1969  Olin ....................................... 71/118

FOREIGN PATENT DOCUMENTS 539  2/1979  European Pat. Off. .
2643477  4/1977  Fed. Rep. of Germany .
2648008  5/1978  Fed. Rep. of Germany .

Primary Examiner—Catherine L. Mills
Attorney, Agent, or Firm—Keil & Witherspoon

[57] ABSTRACT

Novel N-azolylacetanilides of the formula

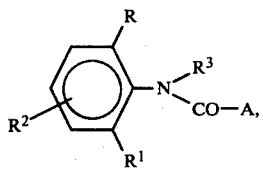

where R denotes hydrogen or $C_1$–$C_4$-alkyl; $R^1$ denotes hydrogen, $C_1$–$C_4$-alkyl or halogen; $R^2$ denotes hydrogen or methyl, $R^3$ denotes unsubstituted or $C_1$–$C_4$-alkoxy-substituted $C_1$–$C_4$-alkyl, $C_3$–$C_4$-alkynyl or A; and A denotes N-azolylmethyl which is unsubstituted or substituted in the heterocyclic ring by from one to three radicals selected from the group consisting of methyl, methoxy and chlorine, processes for their manufacture, and their use as herbicides.

3 Claims, No Drawings

N-AZOLYL ACETANILIDES, THE MANUFACTURE THEREOF, AND THEIR USE AS

The present invention relates to novel N-azolylacetanilides, processes for their manufacture, and their use as herbicides.

The use of N-azolylmethylchloracetanilides as herbicides has been disclosed (German Laid-Open Application DE-OS No. 2,648,008).

We have found that new N-azolylacetanilides of the formula

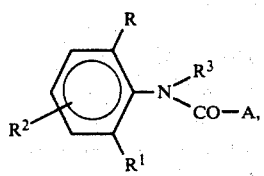

where R denotes hydrogen or $C_1$–$C_4$-alkyl; $R^1$ denotes hydrogen, $C_1$–$C_4$-alkyl or halogen; $R^2$ denotes hydrogen or methyl, $R^3$ denotes unsubstituted or $C_1$–$C_4$-alkoxy-substituted $C_1$–$C_4$-alkyl, $C_3$–$C_4$-alkynyl or A; and A denotes N-azolylmethyl which is unsubstituted or substituted in the heterocyclic ring by from one to three radicals selected from the group consisting of methyl, methoxy and chlorine, have herbicidal effects and exhibit a growth-regulating action.

These compounds are tolerated extremely well by crop plants.

We have further found that N-azolylacetanilides of the formula I are obtained when a 2-haloacetanilide of the formula

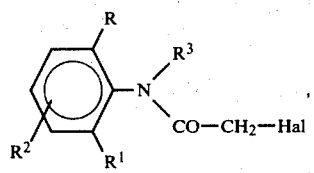

where R, $R^1$, $R^2$ and $R^3$ have the above meanings and Hal denotes halogen, especially chlorine or bromine, is reacted with an azole of the formula

M-B     III, where M denotes hydrogen or an alkali metal and B denotes azole which is unsubstituted or substituted by from one to three radicals selected from the group consisting of methyl, methoxy and chlorine, in the presence or absence of an agent which binds hydrogen halide and in the presence or absence of a solvent inert to the reactants (Process A).

We have further found that the above reaction can, when M is hydrogen, advantageously be carried out in a 2-phase system, the one phase being aqueous alkali and the other a solvent immiscible with the aqueous phase and inert under the reaction conditions, in the presence of a phase transfer catalyst (Process B).

We have still further found that N-azolylacetanilides of the formula I are obtained by reaction of an aniline of the formula

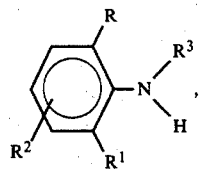

where R, $R^1$, and $R^2$ have the above meanings and $R^3$ denotes $C_2$–$C_4$-alkyl which is unsubstituted or substituted at the 2-position carbon by $C_3$–$C_4$-alkoxy, or $R^3$ denotes $C_3$–$C_4$-alkynyl, with an N-azolylacetic acid halide of the formula B-CH$_2$-CO-Hal     V, where B and Hal have the above meanings, in the presence or absence of a diluent and in the presence or absence of an acid binder (Process C).

Process A is preferred.

By alkyl and alkyl portion of alkoxy in radicals R, $R^1$, $R^2$ and $R^3$, we mean for instance-depending on the number of carbon atoms stated-the following groups: methyl, ethyl, n-propyl, isopropyl, and n-, iso-, sec- and tert-butyl.

Propargyl and butyn-1-yl-3 may be mentioned as examples of $C_3$–$C_4$-alkynyl. Halogen should be taken to mean chlorine, bromine and iodine, especially chlorine. By the N-azolylmethyl radical A, we mean for instance azoles linked to the ring nitrogen via a methyl group, such as pyrazole, imidazole, 1,2,4-triazole or 1,2,3-triazole, and their representative substituted on the ring carbon atom by from one to three radicals selected from the group consisting of methyl, methoxy or chlorine, e.g., 4-methylpyrazole, 4-methoxypyrazole, 4-chloropyrazole, 3,5-dimethylpyrazole, 3(5)-methylpyrazole, 3(5)-methyl-1,2,4-triazole, 3,5-dimethyl-1,2,4-triazole, 4,5-dimethyl-1,2,3-triazole, 2-methylimidazole, 4,5-dichloroimidazole and 2-methyl-4,5-dichloroimidazole.

Processes A and C may be carried out in the presence or absence of solvents to which the reactants are inert. Suitable examples for process A are aromatic hydrocarbons, such as toluene and xylene; halohydrocarbons, such as chlorobenzene, dichlorobenzene, and carbon tetrachloride; ethers, such as tetrahydrofuran and dioxane; nitriles, such as acetonitrile; and N,N-dialkylamides, such as dimethylformamide, or sulfones, such as dimethyl sulfoxide, and water, and mixtures of such solvents, when M is hydrogen. The hydrogen halide which is liberated may be bound by acid binders, such as tertiary amines, e.g., triethylamine, pyridine and pyridine bases, or by using at least twice the molar amount of azole H-B. If alkali metal salts of the azoles are used as reactants, it is advantageous to employ aprotic polar solvents, such as N,N-dialkylamides, e.g., dimethylformamide, nitriles, e.g., acetonitrile, or sulfones, e.g., dimethyl sulfoxide. The reaction temperatures are from 0° to 200° C., preferably from 25° to 150° C. At least molar amounts of azole and acid binder, or at least molar amounts of an alkali metal salt of the azole, are used, based on 2-haloacetanilide employed.

In Process B, the N-azolylacetanilides of the formula I are produced in a 2-phase system, the one phase being aqueous alkali and the other a solvent immiscible with water and inert under the rection conditions, e.g., an aromatic hydrocarbon or a halohydrocarbon. A phase transfer catalyst is added to the 2-phase system in amounts of from 0.5 to 30 mole%, based on 2-haloacetanilide of the formula I employed. Suitable phase transfer catalysts are onium compounds, e.g., quaternary ammonium or phosphonium compounds, or macrocyclic polyethers. Reaction temperatures are from 0° to 150° C., preferably from 25° to 100° C. At least molar amounts of azole and alkali, based on 2-haloacetanilide of the formula II employed, are used.

In Process C, for example from 1 to 4 moles of N-azolylacetic said halide V, which is manufactured in situ, and from 1 to 2 moles of acid binder are used per mole of aniline of the formula IV. Suitable solvents are those given for Process A, with the exception of water. Suitable acid binders are the compounds given for Process A.

To isolate the compounds of the formula I, the halide is if desired filtered off, the filtrate or the suspension is evaporated, and the residue is taken up in an organic, water-immiscible solvent. The organic phase is washed with water, dried and concentrated under reduced pressure. The product of the formula I thus obtained is in many instances pure; if necessary, it may be further purified by recrystallization from a suitable solvent or by chromatography using silica gel.

The 2-haloacetanilides of the formula II used as starting compounds are known compounds (e.g., German No. 1,014,380, German Printed Applications DE-AS No. 2,305,495, DE-AS No. 2,328,340 and DE-AS No. 1,543,751, German Laid-Open Application DE-OS No. 2,648,008 and German Printed Applications DE-AS No. 2,362,743 and DE-AS No. 1,542,702).

The anilides of the formula IV are also known from the literature (e.g., German Printed Applications DE-AS Nos. 2,305,495; 2,328,340; 1,542,702; and 2,362,743).

The compounds of the formula V are described as acids in JACS, 77, 622, 1955.

The following examples illustrate the preparation of the novel N-azolylacetanilides, without restricting the processes according to the invention to them. In the examples, parts by weight bear the same realtionship to parts by volume as kilograms to liters.

EXAMPLE 1 (Process B)

27.8 parts by weight of 2-chloro-2',6'-dimethyl-N-(pyrazol-1-yl-methyl)-acetanilide dissolved in 50 parts by volume of toluene, and 8.1 parts by weight of pryazole, 4.0 parts by weight of sodium hydroxide and 2.0 parts by weight of benzyltriethylammonium chloride dissolved in 20 parts by volume of water are intensively mixed for 8 hours at 80° C. The organic phase is then separated, 60 parts by volume of methylene chloride is added, and the mixture is washed 3 times, each time with 100 parts by volume of water, and dried over sodium sulfate. After the solvents have been evaporated under reduced pressure and the residue has been recrystallized from 40 parts by volume of toluene, 25.0 parts by weight of N-(pyrazol-1-yl-methyl-pyrazol)-1-yl-acetic acid-2',6'-diemthylanilide of melting point 133° C. is isolated.

$C_{17}H_{19}N_5O$ (M 309): calc.: C 66.0, H 6.1, N 22.6; found: C 66.1, H 5.8, N 22.4.

EXAMPLE 2 (Process A)

7.6 parts by weight of triazole is dissolved in 17.5 parts by weight of 30% methanolic sodium methylate solution, the solution is concentrated to dryness under reduced pressure, and the residue is dissolved in 80 parts by volume of dimethylformamide. 28.4 parts by weight of N-(3'-methoxypropyl-(2'))-2-methyl-6-ethyl-chloroacetanilide is added and the mixture is heated for 3 hours at 40° C., with stirring. After the solvent has been evaporated off under reduced pressure, the residue is taken up in methylene chloride and washed 3 times with water. After removal of the solvent under reduced pressure and pasting of the crystalline residue with petroleum ether, 22.8 parts by weight of N-(3'-methoxypropyl-(2')-1,2,4-triazol-1-yl-acetic acid-2''-methyl-6''-ethylanilide of melting point 69°–71° C. is obtained.

$C_{17}H_{24}N_4O_2$ (M 316): calc: C 64.5, H 7.6, N 17.7; found: C 64.4, H 7.6, N 17.6.

EXAMPLE 3 (Process A)

13.8 parts by weight of 2-chloro-2',6'-dimethyl-N-(pyrazol-1-yl-methyl)-acetanilide, 17.0 parts by weight of imidazole, 15 parts by volume of dioxane, and 50 parts by volume of water are refluxed for 20 hours and then concentrated under reduced pressure. The residue is extracted 3 times, each time with 80 parts by volume of ethyl acetate. The organic phase are combined and washed with 100 parts by volume of water, and the solution is filtered through a silica gel column. After evaporation of the solvent, there is isolated from the eluate 7.5 parts by weight of N-(pyrazol-1-yl-methyl)-imidazol-1-yl-acetic acid-2',6'-dimethylanilide as an oil ($n_D^{25}$: 1.5505).

$C_{17}H_{19}N_5O$ (M 309).

EXAMPLE 4 (Process C)

At 30° C. to 40° C., 1 drop of dimethylformamide is added to 8.6 parts by weight of 1,2,4-triazol-1-yl-acetic acid dispersed in 25 parts by volume of toluene; subsequently, 12.7 parts by weight of oxalyl chloride is dripped in and the mixture is stirred for 3 hours at the same temperature. The precipitate which forms (hydrochloride of the acid chloride) is filtered, washed twice, each time with 20 parts by volume of toluene, and dissolved in 60 parts by volume of toluene; after the addition of 3.4 parts by weight of N-isopropylaniline and 6.9 parts by weight of potassium carbonate, the mixture is stirred for 12 hours at 100° C. After cooling and distribution of the mixture between 50 parts by volume of ethyl acetate and 50 parts by volume of water, 5.0 parts by weight of N-isopropyl-1,2,4-triazol-1-yl-acetanilide of melting point 125° C. is isolated from the organic phase.

The following compounds are prepared analogously (Process A or B):

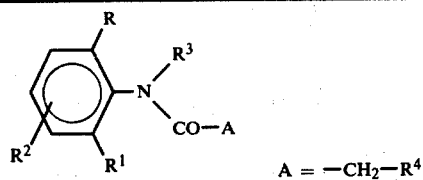

$A = -CH_2-R^4$

| Compound no. | R | $R^1$ | $R^2$ | $R^3$ | $R^4$ | m.p. $n_D^{25}$, b.p. |
|---|---|---|---|---|---|---|
| 1 | H | H | H | $CH_2$-N(pyrazolyl) | -N(pyrazolyl) | 82 |
| 2 | H | H | H | " | -N(4,5-dichloroimidazolyl) | 150 |
| 3 | H | H | H | " | -N(1,2,4-triazolyl) | |
| 4 | H | H | H | $CH_2$-N(1,2,4-triazolyl) | -N(1,2,4-triazolyl) | |
| 5 | H | H | H | " | -N(pyrazolyl) | |
| 6 | $CH_3$ | $CH_3$ | H | $CH_2$-N(pyrazolyl) | " | 133 |
| 7 | $CH_3$ | $CH_3$ | H | " | -N(1,2,4-triazolyl) | viscous |
| 8 | $CH_3$ | $CH_3$ | H | " | -N(imidazolyl) | 1.5505 |
| 9 | $CH_3$ | $CH_3$ | H | $CH_2$-N(pyrazolyl) | -N(4,5-dichloroimidazolyl) | 179 |
| 10 | $CH_3$ | $CH_3$ | 3-$CH_3$ | " | -N(pyrazolyl) | |
| 11 | $CH_3$ | $CH_3$ | 3-$CH_3$ | " | -N(1,2,4-triazolyl) | |
| 12 | $CH_3$ | $CH_3$ | H | $CH_2$-N(imidazolyl) | -N(pyrazolyl) | |
| 13 | $CH_3$ | $CH_3$ | H | " | -N(1,2,4-triazolyl) | |

-continued

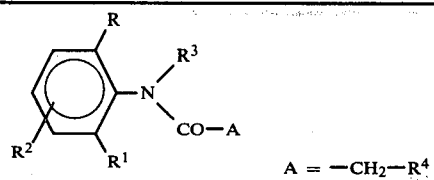

A = —CH$_2$—R$^4$

| Compound no. | R | R$^1$ | R$^2$ | R$^3$ | R$^4$ | m.p. n$_D^{25}$, b.p. |
|---|---|---|---|---|---|---|
| 14 | CH$_3$ | CH$_3$ | H | CH$_2$—N(imidazole-4,5-diCl) | pyrazol-1-yl | |
| 15 | CH$_3$ | CH$_3$ | H | " | 1,2,4-triazol-1-yl | |
| 16 | CH$_3$ | C$_2$H$_5$ | H | CH$_2$—N(1,2,4-triazol-1-yl) | pyrazol-1-yl | 122 |
| 17 | CH$_3$ | C$_2$H$_5$ | H | " | imidazole-4,5-diCl | 115 |
| 18 | CH$_3$ | C$_2$H$_5$ | H | " | 1,2,4-triazol-1-yl | |
| 19 | CH$_3$ | C$_2$H$_5$ | H | CH$_2$—N(pyrazol-1-yl) | pyrazol-1-yl | |
| 20 | CH$_3$ | C$_2$H$_5$ | H | " | 1,2,4-triazol-1-yl | |
| 21 | C$_2$H$_5$ | C$_2$H$_5$ | H | " | " | |
| 22 | H | H | H | CH(CH$_3$)$_2$ | pyrazol-1-yl | 133 |
| 23 | H | H | H | " | 1,2,4-triazol-1-yl | 125 |
| 24 | H | H | H | " | 4-methylpyrazol-1-yl | |
| 25 | H | H | H | CH(CH$_3$)C≡CH | pyrazol-1-yl | 88 |
| 26 | H | H | H | " | 1,2,4-triazol-1-yl | 141 |
| 27 | H | H | H | CH$_2$C≡CH | pyrazol-1-yl | |

-continued

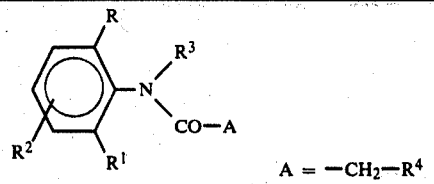

A = —CH$_2$—R$^4$

| Compound no. | R | R$^1$ | R$^2$ | R$^3$ | R$^4$ | m.p. n$_D^{25}$, b.p. |
|---|---|---|---|---|---|---|
| 28 | H | H | H | " | 1,2,4-triazol-1-yl | |
| 29 | CH$_3$ | C$_2$H$_5$ | H | H | pyrazol-1-yl | |
| 30 | CH$_3$ | C$_2$H$_5$ | H | H | 1,2,4-triazol-1-yl | |
| 31 | CH$_3$ | CH$_3$ | H | CH$_2$OCH$_3$ | pyrazol-1-yl | 65 |
| 32 | CH$_3$ | CH$_3$ | H | " | 4,5-dichloroimidazol-1-yl | 152 |
| 33 | CH$_3$ | CH$_3$ | H | " | 1,2,4-triazol-1-yl | |
| 34 | CH$_3$ | C$_2$H$_5$ | H | CH$_2$OC$_2$H$_5$ | 1,2,4-triazol-1-yl | |
| 35 | CH$_3$ | C$_2$H$_5$ | H | CH$_2$OC$_2$H$_5$ | pyrazol-1-yl | |
| 36 | C$_2$H$_5$ | C$_2$H$_5$ | H | CH$_2$OCH$_3$ | " | 98 |
| 37 | C$_2$H$_5$ | C$_2$H$_5$ | H | " | 1,2,4-triazol-1-yl | 51 |
| 38 | C$_2$H$_5$ | C$_2$H$_5$ | H | " | 4,5-dichloroimidazol-1-yl | 114 |
| 39 | C$_2$H$_5$ | C$_2$H$_5$ | H | CH$_2$OC$_4$H$_9$ | pyrazol-1-yl | |
| 40 | C$_2$H$_5$ | C$_2$H$_5$ | H | " | imidazol-1-yl | |
| 41 | CH$_3$ | CH$_3$ | H | CH$_2$CH$_2$OCH$_3$ | pyrazol-1-yl | 160/0.01 |

-continued

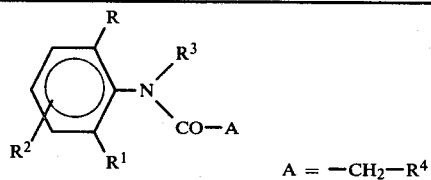

A = —CH₂—R⁴

| Compound no. | R | R¹ | R² | R³ | R⁴ | m.p. $n_D^{25}$, b.p. |
|---|---|---|---|---|---|---|
| 42 | CH₃ | CH₃ | H | " | −N−N=\\N | 1.5319 |
| 43 | CH₃ | CH₃ | H | " | −N−N=\\N, Cl, Cl | 116 |
| 44 | CH₃ | CH₃ | H | CH(CH₃)CH₂OCH₃ | −N−N=\\ | |
| 45 | CH₃ | CH₃ | H | " | −N−N=\\N | |
| 46 | CH₃ | C₂H₅ | H | " | −N−N=\\ | 1.5385 |
| 47 | CH₃ | C₂H₅ | H | " | −N−N=\\N | 71 |

The new active ingredients may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The influence of the new compounds on the growth of plants is demonstrated in the following greenhouse experiments.

The vessels employed were plastic flowerpots having a volume of 300 cm$^3$, and which were filled with a sandy loam containing about 1.5% humus. The seeds of the test plants (cf. Table 1) were sown shallow, and separately, according to species. In the case of Cyperus esculentus, pregerminated tubers were used. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals, and prevented readily volatile active ingredients from evaporating.

For postemergence treatment, the plants were first grown to a height of 3 to 10 cm, depending on the growth shape, before being treated. The vessels were not covered after treatment. The pots were set up in the greenhouse—species from warmer areas at from 25° to 40° C., and species from moderate climates at 15° to 30° C. The experiments were run for 4 weeks. During this period, the plants were tended and their reactions to the various treatments assessed. The following tables containg the compounds investigated, the applications rates in kg/ha of active ingredient, and the plants used for the tests. The scale used for assessment was 0 to 100, 0 denoting no damage or normal emergence, and 100 denoting nonemergence or complete destruction of at least the visible plant parts.

The enclosed tables show the results obtained. Postemergence application in particular afforded, in addition to combating other unwanted plants, remarkably successful control of Cyperus esculentus (a weed of considerable significance in agriculture), without damaging, at the application rates employed, important crop plants.

In addition to surface application, the active ingredients may also be incorporated into the soil either before or after the crop plants are sown, or between already existing crop plants.

If the crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

Further, the active ingredients may be employed where it is desired merely to slow down grass growth without killing the plants.

In view of the many application methods possible, the agents according to the invention, or mixtures containing them, may be used not only on the crop plants listed in the tables, but also in a much larger range of crops for removing unwanted plants. Depending on the object to be achieved, the application rates vary from 0.1 to 15 kg/ha and more.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapas* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Dancus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |

-continued

| Botanical name | Common name |
|---|---|
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

The new compounds may also be used as growth-regulating agents for plants, e.g., for reducing growth height. Application rates for this purpose are for example from 0.01 to 10 kg/ha.

The new acetanilides according to the invention may be mixed with each other, combined with prior art haloacetanilides, or mixed with numerous representatives of other herbicidal or growth-regulating active ingredient groups, and applied in such combinations. These combinations extend the spectrum of action, and synergistic effects are sometimes achieved. Examples of such compounds which may be admixed are given below:

| R | R$^1$ | R$^2$ |
|---|---|---|
|  | NH$_2$ | Cl |
|  | NH$_2$ | Br |
|  | OCH$_3$ | OCH$_3$ |
| 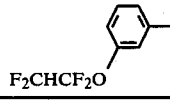 | —N(CH$_3$)$_2$ | Cl |
| 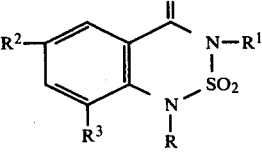 | OCH$_3$ | OCH$_3$ |
| 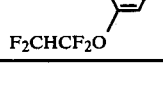 | NH$_2$ | Cl |
| 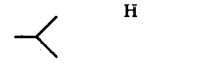 | —N(CH$_3$)$_2$ | Cl |
|  | NHCH$_3$ | Cl |
|  | OCH$_3$ | Cl |
| 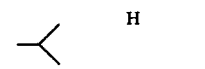 | NH$_2$ | Br |
|  | OCH$_3$ | OCH$_3$ |
| 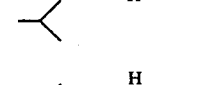 | NH.CH$_3$ | Cl |

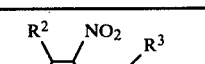

| R | R$^1$ | R$^2$ | R$^3$ |
|---|---|---|---|
| H | isopropyl | H | H (salts) |
| H | isopropyl | H | CH$_3$ (salts) |
| H | isopropyl | H | Cl (salts) |
| CH$_2$—OCH$_3$ | isopropyl | H | H |
| H | isopropyl | H | F (salts) |
| CH$_2$—OCH$_3$ | isopropyl | H | Cl |
| CH$_2$—OCH$_3$ | isopropyl | H | F |
| CN | isopropyl | H | Cl |

| R | R$^1$ | R$^2$ | R$^3$ | R$^4$ |
|---|---|---|---|---|
| H | H$_3$CSO$_2$ | H | n.C$_3$H$_7$ | n.C$_3$H$_7$ |
| H | F$_3$C | H | C$_2$H$_5$ | C$_4$H$_9$ |
| H | F$_3$C | H | n.C$_3$H$_7$ | n.C$_3$H$_7$ |

-continued

| | | | | |
|---|---|---|---|---|
| H | F₃C | H | —CH₂—CH₂Cl | n.C₃H₇ |
| H | tert C₄H₉ | H | sec C₄H₉ | sec C₄H₉ |
| H | SO₂NH₂ | H | n.C₃H₇ | n.C₃H₇ |
| H | F₃C | H | n.C₃H₇ | —CH₂—⟨cyclopropyl⟩ |
| H₃C | H₃C | H | H | sec C₄H₉ |
| H₃C | H₃C | H | H | —CH(C₂H₅)₂ |
| H | F₃C | NH₂ | n.C₃H₇ | n.C₃H₇ |
| H | H₃C | H | n.C₃H₇ | n.C₃H₇ |
| H | iC₃H₇ | H | n.C₃H₇ | n.C₃H₇ |

$$\overset{R^1}{\underset{R^2}{N}}-\overset{}{\underset{O}{C}}-O-R^2$$

| R | R¹ | R² |
|---|---|---|
| phenyl | H | iC₃H₇ |
| CH₃ | H | —CH₂—(3,4-Cl₂-C₆H₃) |
| 3-Cl-C₆H₄— | H | —CH(CH₃)—C≡CH |
| 3-Cl-C₆H₄— | H | —CH₂—C≡C—CH₂Cl |
| 3-Cl-C₆H₄— | H | iC₃H₇ |
| phenyl | H | —CH(CH₃)—C(O)—NH—C₂H₅ |
| 3,4-Cl₂-C₆H₃— | H | CH₃ |
| H₂N—C₆H₄—SO₂— | H | CH₃ |
| CH₃ | H | tert H₉C₄—(2,4-di-tert-C₄H₉-5-CH₃-C₆H₂) |
| phenyl | H | —N=C(CH₃)₂ |

-continued $$R-\overset{R^1}{\underset{}{N}}-\overset{}{\underset{O}{C}}-O-\langle C_6H_3(NHC(O)OR^2)\rangle$$

| R | R¹ | R² |
|---|---|---|
| | H | CH₃ |
| 3-CH₃-C₆H₄— | | |
| phenyl | H | C₂H₅ |
| 3,5-(CH₃)₂-C₆H₃— | H | C₂H₅ |
| phenyl | CH₃ | CH₃ |
| 4-F-C₆H₄— | H | CH₃ |
| 4-F-C₆H₄— | H | C₂H₅ |
| 3,4-F₂-C₆H₃— | H | C₂H₅ |
| 3-Cl-4-F-C₆H₃— | H | C₂H₅ |
| 3,4-F₂-C₆H₃— | H | CH₃ |
| 3-Cl-4-F-C₆H₃— | H | CH₃ |

3-CF₃-C₆H₄—NH—C(O)—O—(2-CH₃-5-NHC(O)OCH₃-C₆H₃)

$$\overset{R^1}{\underset{R}{N}}-\overset{}{\underset{O}{C}}-S-R^2$$

| R | R¹ | R² |
|---|---|---|
| iC₃H₇ | iC₃H₇ | CH₂—CCl=CCl₂ |
| iC₃H₇ | iC₃H₇ | CH₂—CCl=CHCl |
| n.C₃H₇ | n.C₃H₇ | C₂H₅ |
| cyclohexyl | C₂H₅ | C₂H₅ |
| sec C₄H₉ | sec C₄H₉ | C₂H₅ |

-continued

| | | |
|---|---|---|
| n.C₃H₇ | n.C₃H₇ | n.C₃H₇ |
| C₂H₅ | C₂H₅ | —CH₂—C₆H₄—Cl |
| sec C₄H₉ | sec C₄H₉ | —CH₂—C₆H₅ |
|  | C₂H₅ | C₂H₅ |
| iC₃H₇ | iC₃H₇ |  |
| iC₃H₇ | iC₃H₇ |  |

R—CH₂—CCl=CHCl
   —CH₂—CCl=CCl₂

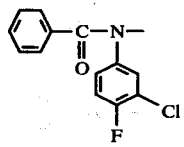

| R | X | Y | R¹ |
|---|---|---|---|
| CH₃ | Cl | Cl | Na |
| 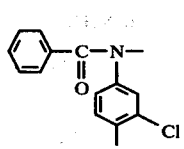 | Cl | H | CH₃ |
| 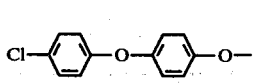 | H | H | H (salts) |
| 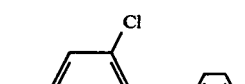 | Cl | Cl | Na |
| | H | CH₃ | CH₃ |
| 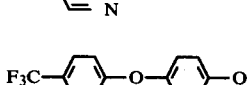 | H | CH₃ | C₂H₅ |
| C₂H₅ | Cl | Cl | Na |

-continued

| | | | |
|---|---|---|---|
| 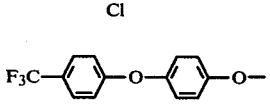 | H | CH₃ | iC₃H₇ |
| 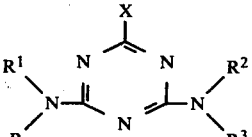 | H | CH₃ | CH₃ |
| 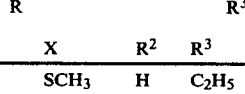 | H | CH₃ | —CH₂—CH(CH₃)₂ |
|  | H | CH₃ | Na |
|  | H | CH₃ | Na |
|  | H | CH₃ | CH₃ |

| R | R¹ | X | R² | R³ |
|---|---|---|---|---|
| H | tert.C₄H₉ | SCH₃ | H | C₂H₅ |
| H | C₂H₅ | SCH₃ | H | C₂H₅ |
| H | iC₃H₇ | SCH₃ | H | C₂H₅ |
| H | CH₃ | SCH₃ | H | iC₃H₇ |
| H | iC₃H₇ | Cl | H | C₂H₅ |
| H | iC₃H₇ | Cl | H | 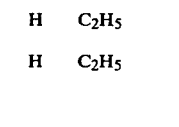 |
| H | C₂H₅ | Cl | H | C₂H₅ |
| H | C₂H₅ | Cl | H | —C(CH₃)₂—CN |
| H | iC₃H₇ | Cl | H | iC₃H₇ |
| H | iC₃H₇ | OCH₃ | H | iC₃H₇ |
| H | —C(CH₃)₂—CN | Cl | H | 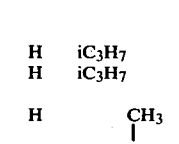 |
| H | C₂H₅ | Cl | H | —CH(CH₃)—CH₂—OCH₃ |
| H | C₂H₅ | Cl | H | —CH(CH₃)—C≡CH |

-continued $$\underset{R}{\overset{R^1}{N}}-\underset{O}{\overset{\|}{C}}-R^2$$

| R | R¹ | R² |
|---|----|----|
| CH₃ | CH₃ | CH(C₆H₅)₂ |
| 1-naphthyl | H | 2-carboxyphenyl (o-COOH-C₆H₄) |
| 3,4-dichlorophenyl | H | cyclopropyl |
| 3,4-dichlorophenyl | H | C₂H₅ |
| 5-chloro-4-methyl-thiazol-2-yl | H | C₂H₅ |
| 4-chlorophenyl | H | -C(CH₃)₂-CH₂-CH₂-CH₃ |

$$\underset{R}{\overset{R^1}{N}}-\underset{O}{\overset{\|}{C}}-R^2$$

| R | R¹ | R² |
|---|----|----|
| phenyl | -CH(CH₃)-C≡CH | CH₂Cl |
| 2-methyl-6-ethylphenyl | -CH(CH₃)-CH₂-OCH₃ | CH₂Cl |
| 2,6-diethylphenyl | -CH₂-OCH₃ | CH₂Cl |
| 2,6-diethylphenyl | -CH₂-C(=O)-OC₂H₅ | CH₂Cl |
| phenyl | iC₃H₇ | CH₂Cl |
| 2,6-dimethylphenyl | -CH₂-O-CH₂-CH(CH₃)-CH₃ | CH₂Cl |

-continued $$\underset{R}{\overset{R^1}{N}}-\underset{O}{\overset{\|}{C}}-R^2$$

| R | R¹ | R² |
|---|----|----|
| 2,6-diethylphenyl | -CH₂-O-C₄H₉n. | CH₂Cl |
| 2,6-diethylphenyl | -CH₂-O-C₂H₅ | CH₂Cl |
| 2,6-dimethylphenyl | -CH₂-(1,3-dioxolan-2-yl) | CH₂Cl |
| 2,6-dimethylphenyl | -CH₂-CH₂-OCH₃ | CH₂Cl |
| 2,6-dimethylphenyl | -CH₂-(4-methylpyrazol-1-yl) | CH₂Cl |
| 2,6-dimethylphenyl | -CH₂-(4-methoxypyrazol-1-yl) | CH₂Cl |
| 2,6-dimethylphenyl | -CH₂-(1,2,4-triazol-1-yl) | CH₂Cl |
| 2,6-dimethylphenyl | -CH₂-(pyrazol-1-yl) | CH₂Cl |
| 2-methyl-6-ethylphenyl | -CH₂-(pyrazol-1-yl) | CH₂Cl |
| 2,6-dimethylphenyl | -CH₂-(3,5-dimethylpyrazol-1-yl) | CH₂Cl |

-continued
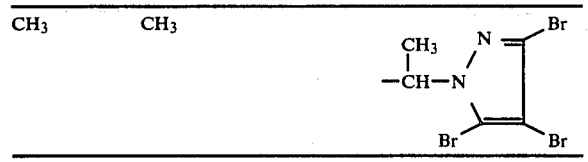
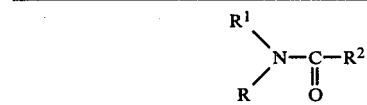
| R | R¹ | R² |
|---|----|----|
| $C_2H_5$ | $C_2H_5$ | 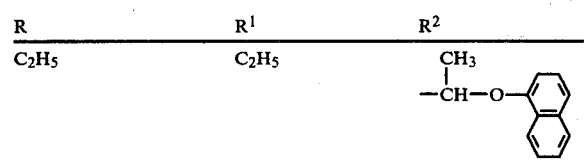 |
| $CH_2=CH-CH_2-$ | $CH_2=CH-CH_2-$ | $CH_2Cl$ |
| 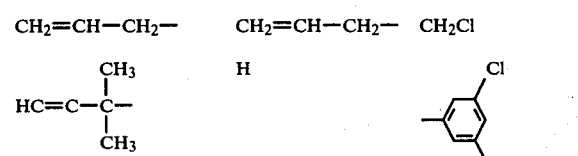 | H | 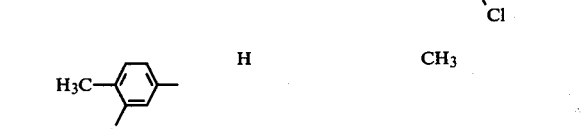 |
|  | H | $CH_3$ |
| 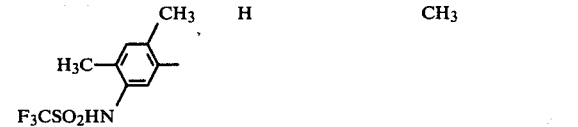 | H | $CH_3$ |
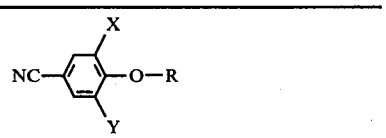
| X | Y | R |
|---|---|---|
| Br | Br | H (salts) |
| I | I | H (salts) |
| Br | Br | $-\underset{\underset{O}{\parallel}}{C}-(CH_2)_6-CH_3$ |
| | | Br salts, esters |
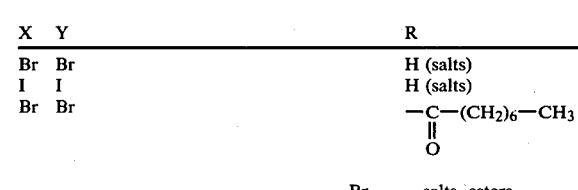
salts, esters
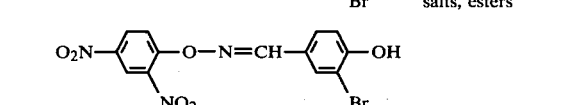
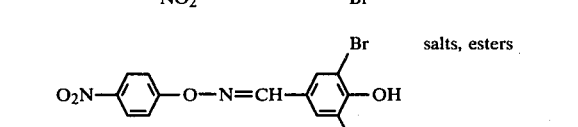
| R | R¹ | R² | R³ |
|---|----|----|----|
| 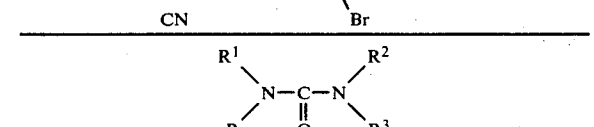 | H | $CH_3$ | $CH_3$ |
| 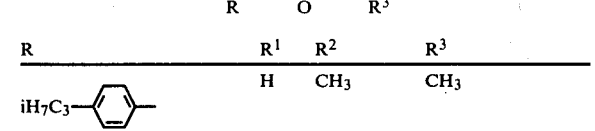 | H | $CH_3$ | $CH_3$ |
-continued
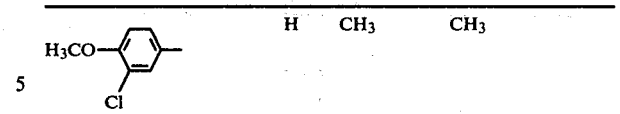
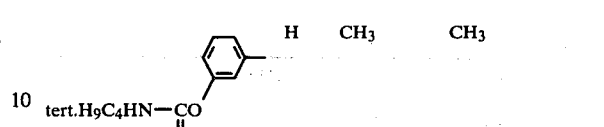
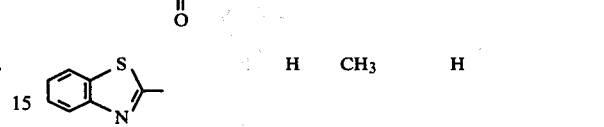
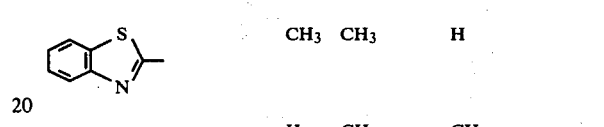
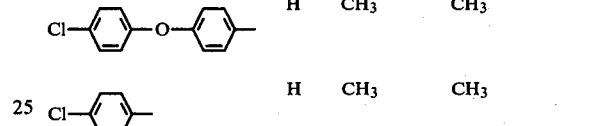
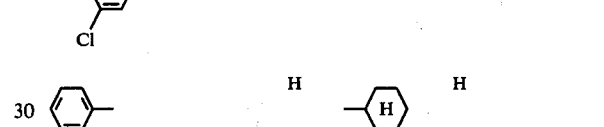
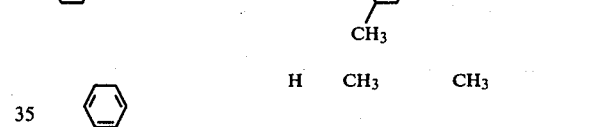
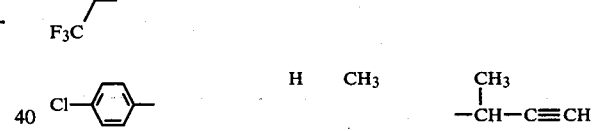
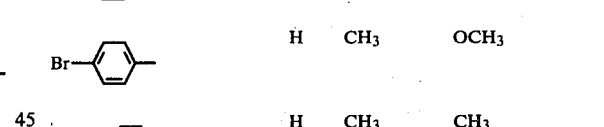
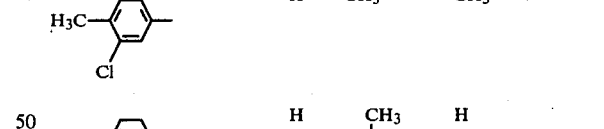
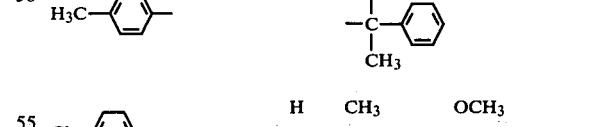
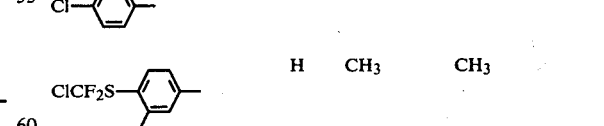
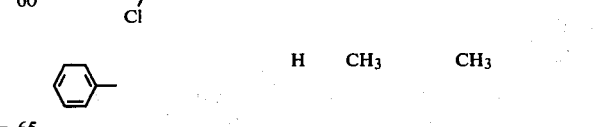
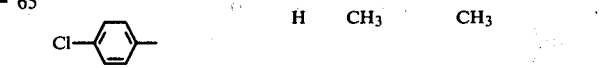

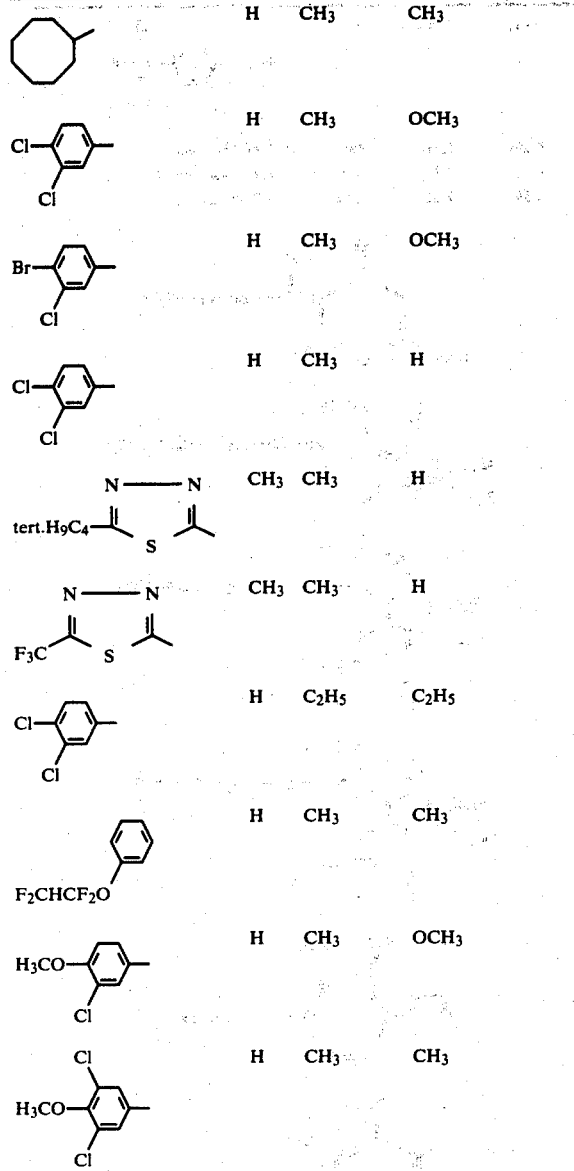
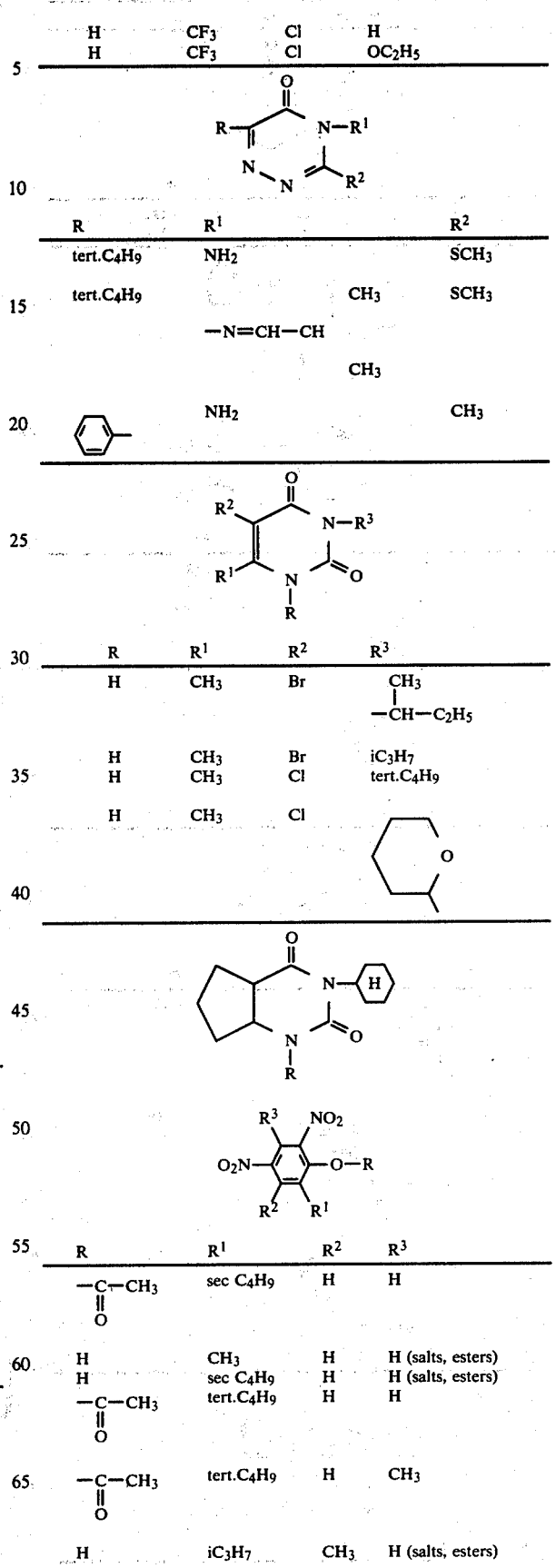

-continued
| | | | |
|---|---|---|---|
| H | tert.C4H9 | H | H (salts) |
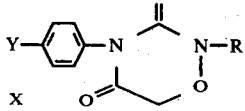
| X | Y | R |
|---|---|---|
| CF3 | H | CH3 |
| H | F | CH3 |
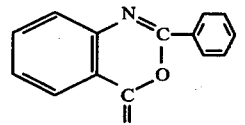
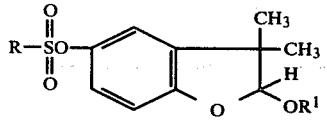
| R | R¹ |
|---|---|
| CH3 | C2H5 |
| $\text{H}_3\text{C}-\text{N}(\text{CH}_3)-$ | C2H5 |
| $\text{H}_3\text{C}-\text{N}(\text{CH}_3)-\text{C}(\text{O})\text{CH}_3$ | C2H5 |
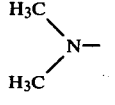
| R | R¹ |
|---|---|
| 3,4-dichlorophenyl | CH3 |
| iH7C3HN-C(O)-O-phenyl | CH3 |
| tert.H9C4HN-C(O)-O-phenyl | CH3 |
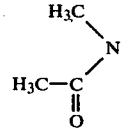
| R | R¹ | R² | X |
|---|---|---|---|
-continued
| | | | |
|---|---|---|---|
| CH3 | CH3 | H | 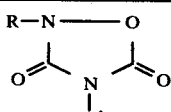 |
| CH3 | CH3 | Br | CH3OSO2O |
| CH3 | CH3 | CH3 | CH3OSO2—O |
| CH3 | CH3 | CH3 | CF3—SO2 |
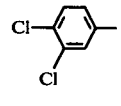
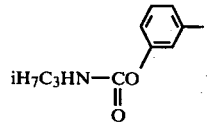
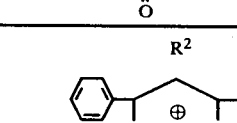
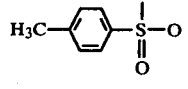 (esters, salts)
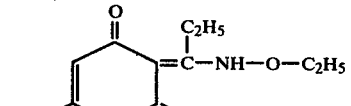 (salts, esters)
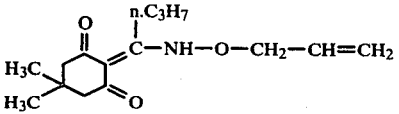
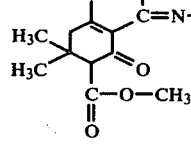
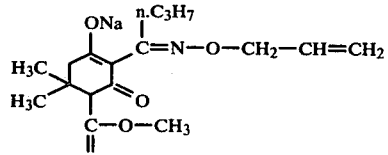 2 Cl⁻

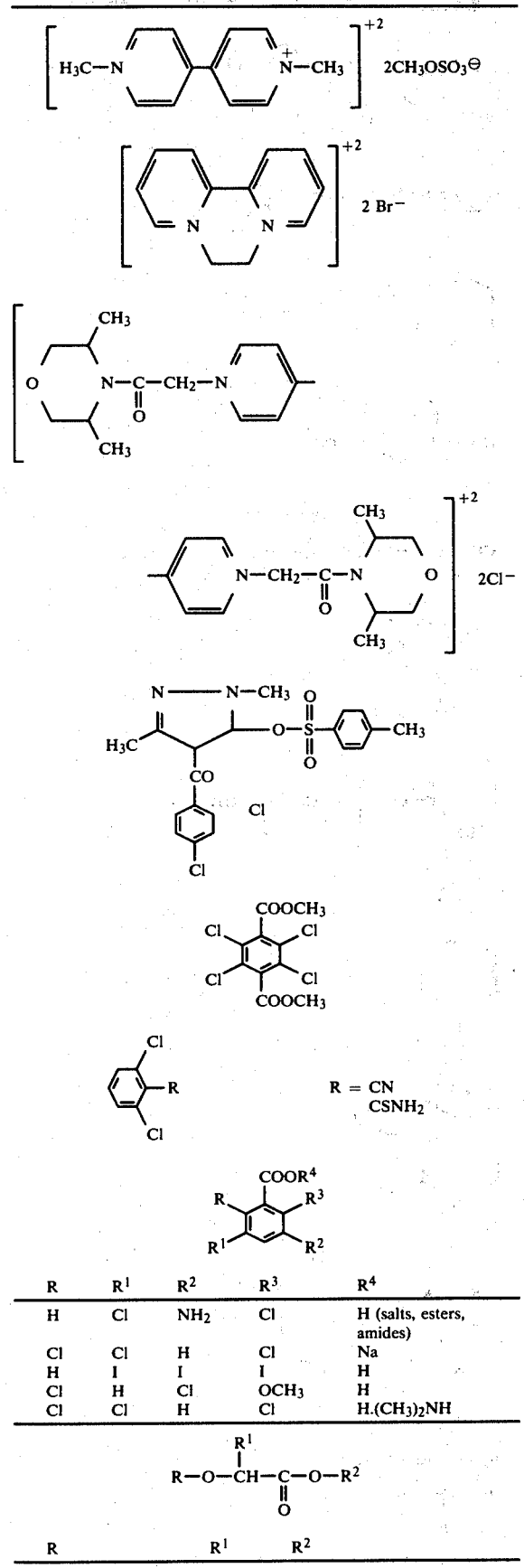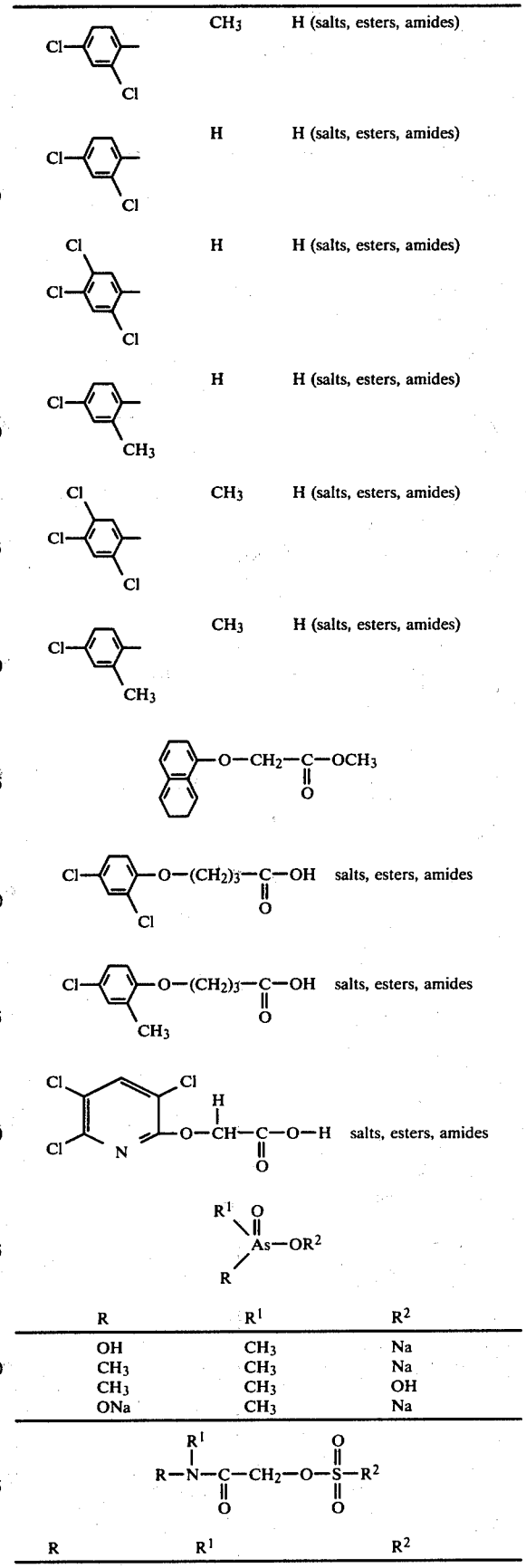

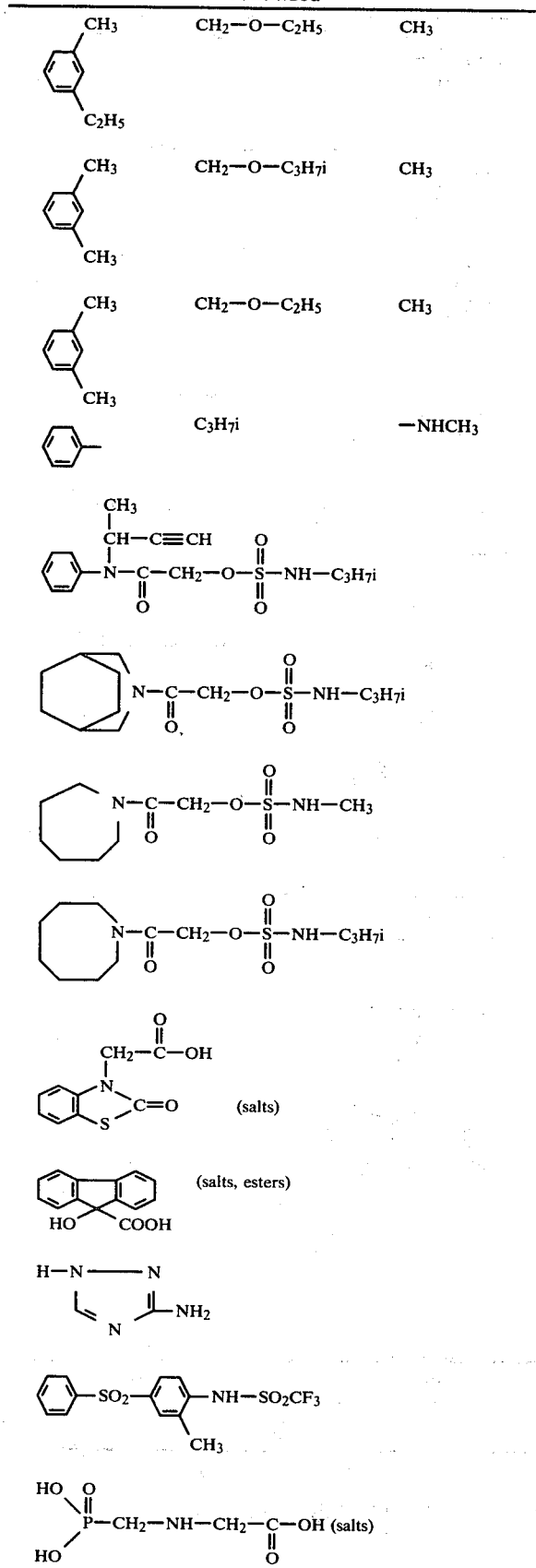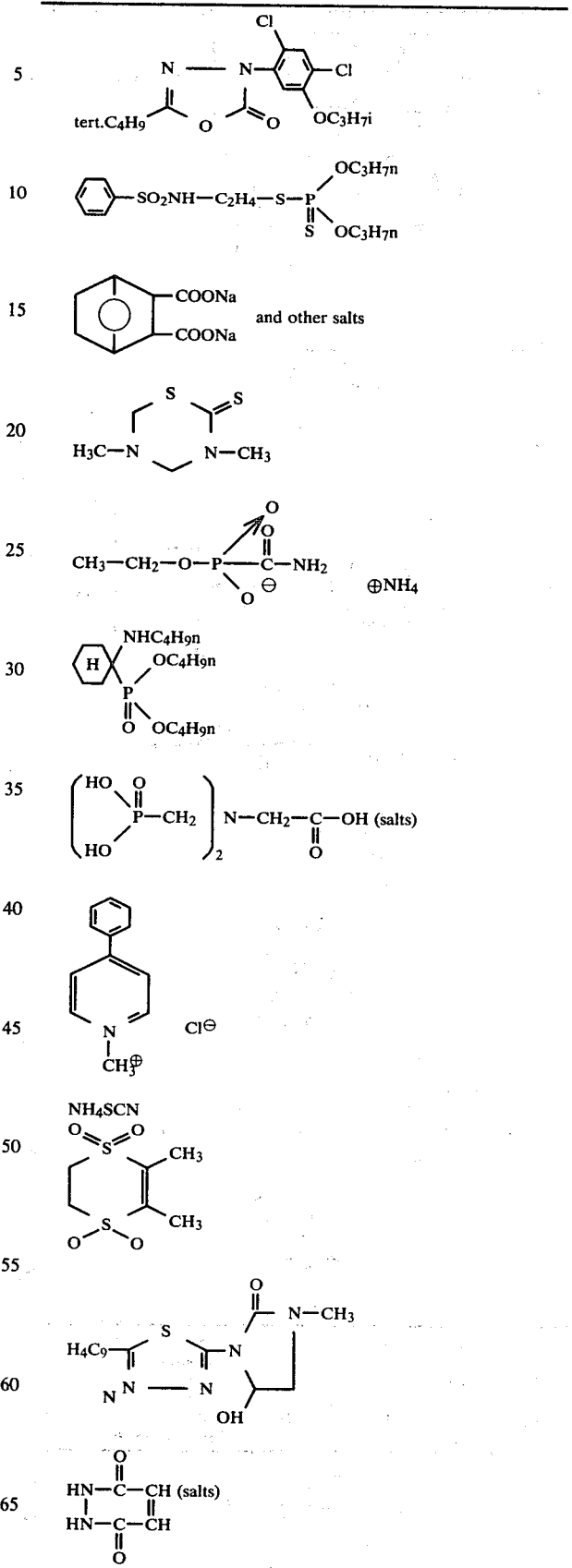

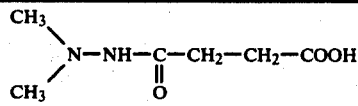

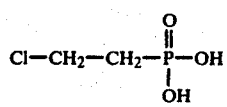

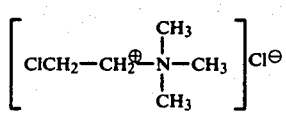

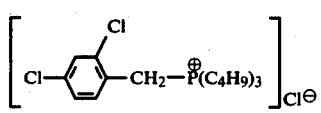

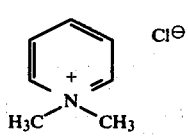

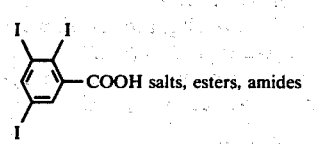

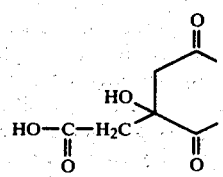

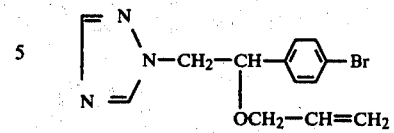

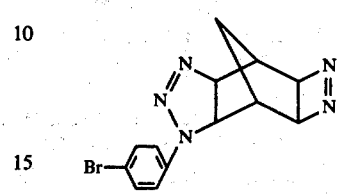

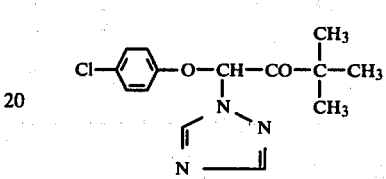

TABLE 1

List of plant names

| Botanical term | Abbreviation in tables | Common name |
|---|---|---|
| Alopecurus myosuroides | — | slender foxtail |
| Amaranthus retroflexus | — | redroot pigweed |
| Beta vulgaris | Beta vulg. | sugar beet |
| Brassica napus | — | rape |
| Bromus tectorum | Bromus tect. | downy brome |
| Cyperus esculentus | Cyper. escul. | yellow nutsedge |
| Echinochloa crus galli | Echin. c.g. | barnyard grass |
| Gossypium hirsutum | Gossyp. hirs. | cotton |
| Sorghum halepense | Sorg. halep. | Johnsongrass |

TABLE 2

Selective control of unwanted grasses in sugarbeets; preemergence treatment in the greenhouse

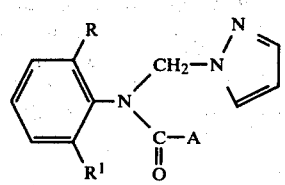

| Compound no. | Substituents A | R | R¹ | kg/ha | Beta vulgaris | Alopecurus myosuroides | Bromus tectorum | Echinochloa crus galli | Amaranthus retroflexus |
|---|---|---|---|---|---|---|---|---|---|
| 7 | | | | 1.0 | 0 | 90 | 90 | 99 | 95 |
| 9 | | | | 2.0 | 0 | — | — | 98 | 85 |
| 6 | | | | 2.0 | 10 | — | 100 | 83 | 97 |
| prior art (German Laid-Open Application DE-OS 2,648,008) | $CH_2Cl$ | $CH_3$ | $CH_3$ | 1.0 | 85 | 100 | 100 | 100 | 100 |

0 = no damage
100 = nonemergence, or plants destroyed

TABLE 3

Suppression of Cyperus and unwanted grasses; postemergence treatment in the greenhouse

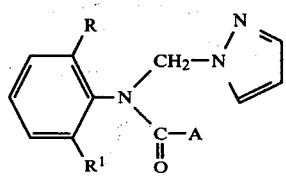

| Compound no. | Substituents A | R | $R^1$ | kg/ha | Beta vulg. | Brassica napus | Gossyp. hirs. | Cyper. escul. | Bromus tect. | Echin. c.g. | Sorgh. halep.[x] |
|---|---|---|---|---|---|---|---|---|---|---|---|
| 7 | | | | 1.0 | 0 | 0 | 0 | 85 | 70 | 75 | 95 |
| | | | | 2.0 | 0 | 0 | 0 | 85 | 80 | 95 | 95 |
| prior art (German Laid-Open Application DE-OS 2,648,008) | $CH_2Cl$ | $CH_3$ | $CH_3$ | 1.0 | 35 | 20 | 18 | 75 | 80 | 92 | 89 |

[x]from seed
0 = no damage
100 = nonemergence, or plants destroyed

TABLE 4

Herbicidal action on preemergence treatment in the greenhouse

| Compound | kg/ha | Test plant and % damage Echinochloa crus-galli |
|---|---|---|
| 16 | 3.0 | 100 |
| 38 | 3.0 | 90 |
| 46 | 3.0 | 100 |

EXAMPLE 4

90 parts by weight of compound 1 is mixed with 10 parts by weight of N-methyl-α-pyrrolidone. A mixture is obtained which is suitable for application in the form of very fine drops.

EXAMPLE 5

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 7

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 9

3 parts by weight of compound 3 is intimately mixed with 97 parts by weight of particulate kaolin. A dust is obtained containing 3% by weight of the active ingredient.

EXAMPLE 10

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

EXAMPLE 12

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An N-azolylacetanilide of the formula

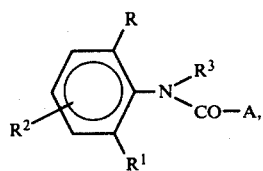

where R denotes hydrogen or $C_1$–$C_4$-alkyl; $R^1$ denotes hydrogen, $C_1$–$C_4$-alkyl or halogen; $R^2$ denotes hydrogen or methyl, $R^3$ denotes A; and A denotes N-azolylmethyl in which the heterocyclic ring of the N-azolylmethyl is a pyrazole, 1,2,4-triazole or imidazole ring which ring is unsubstituted or substituted by from one to three radicals selected from the group consisting of methyl, methoxy and chlorine, with the proviso that both of the heterocyclic rings cannot be imidazole.

2. An N-azolylacetanilide selected from the group consisting of N-(1,2,4-triazol-1-yl-methyl)-pyrazol-1-yl-acetic acid-2',6'-dimethylanilide and N-(pyrazol-1-yl-methyl)-pyrazol-1-yl-acetic acid-2',6'-dimethylanilide.

3. The N-azolylacetanilide of claim 1 which is N-(pyrazol-1-yl-methyl)-pyrazol-1-yl-acetic acid-2',6'-dimethylanilide.

* * * * *

UNITED STATES PATENT AND TRADEMARK OFFICE
CERTIFICATE OF CORRECTION

PATENT NO. : 4,394,513
DATED : July 19, 1983
INVENTOR(S) : Karl Eicken et al.

It is certified that error appears in the above-identified patent and that said Letters Patent is hereby corrected as shown below:

IN THE TITLE

The title should read: N-AZOLYL ACETANILIDES, THE MANUFACTURE THEREOF, AND THEIR USE AS HERBICIDES Signed and Sealed this Fourth Day of October 1983

[SEAL]

Attest:

Attesting Officer

GERALD J. MOSSINGHOFF

Commissioner of Patents and Trademarks